United States Patent [19]

Breillatt, Jr. et al.

[11] Patent Number: 5,728,306

[45] Date of Patent: Mar. 17, 1998

[54] LEUKODEPLETION FILTER AND METHOD FOR FILTERING LEUKOCYTES FROM FRESHLY DRAWN BLOOD

[75] Inventors: Julian P. Breillatt, Jr., Mundelein; Sharon L. Pokropinski, Schaumburg, both of Ill.

[73] Assignee: Baxter International Inc., Deerfield, Ill.

[21] Appl. No.: 370,772

[22] Filed: Dec. 23, 1994

[51] Int. Cl.$^6$ .............. B01D 37/00; B01D 39/00; B01D 39/02; B01D 36/02

[52] U.S. Cl. .............. 210/767; 210/323.1; 210/483; 210/488; 210/489; 210/490; 210/491; 210/496; 210/503; 210/505; 210/507; 210/508; 210/806

[58] Field of Search .............. 210/323.1, 483, 210/484, 488, 489, 490, 491, 492, 496, 503, 505, 507, 508, 767, 806, 314

[56] References Cited

U.S. PATENT DOCUMENTS

| | | | |
|---|---|---|---|
| 4,053,420 | 10/1977 | Marx | 210/435 |
| 4,130,642 | 12/1978 | Kikugawa et al. | |
| 4,157,967 | 6/1979 | Meyst et al. | 210/503 |
| 4,256,588 | 3/1981 | Hoehn et al. | 210/692 |
| 4,283,289 | 8/1981 | Meyst et al. | 210/448 |
| 4,330,410 | 5/1982 | Takenaka et al. | 210/767 |
| 4,416,777 | 11/1983 | Kuroda et al. | 210/446 |
| 4,596,657 | 6/1986 | Wisdom | 210/206 |
| 4,618,533 | 10/1986 | Steuck | |
| 4,701,267 | 10/1987 | Watanabe et al. | 210/806 |
| 4,767,541 | 8/1988 | Wisdom | 210/749 |
| 4,810,378 | 3/1989 | Carmen et al. | 210/206 |
| 4,855,063 | 8/1989 | Carmen et al. | 210/749 |
| 4,880,548 | 11/1989 | Pall et al. | 210/767 |
| 4,915,848 | 4/1990 | Carmen et al. | 210/749 |
| 4,917,799 | 4/1990 | Masuda et al. | 210/435 |
| 4,919,823 | 4/1990 | Wisdom | 210/749 |
| 4,925,572 | 5/1990 | Pall | 210/767 |
| 4,936,993 | 6/1990 | Nomura | 210/446 |
| 4,936,998 | 6/1990 | Nishimura et al. | 210/496 |
| 4,943,287 | 7/1990 | Carmen | 604/6 |
| 4,976,861 | 12/1990 | Pall | 210/508 |
| 4,985,153 | 1/1991 | Kuroda et al. | 210/782 |
| 4,997,577 | 3/1991 | Stewart | 210/767 |
| 5,089,146 | 2/1992 | Carmen et al. | 210/782 |
| 5,092,996 | 3/1992 | Spielberg | 210/435 |
| 5,100,551 | 3/1992 | Pall et al. | 210/486 |
| 5,100,564 | 3/1992 | Pall et al. | 210/767 |
| 5,104,788 | 4/1992 | Carmen et al. | 210/782 |

(List continued on next page.)

FOREIGN PATENT DOCUMENTS

| | | |
|---|---|---|
| 58983/90 | 1/1991 | Australia . |
| 0 370 584 | 5/1990 | European Pat. Off. . |
| 0 397 403 | 11/1990 | European Pat. Off. . |
| 0 406 485 | 1/1991 | European Pat. Off. . |
| 0 408 462 | 1/1991 | European Pat. Off. . |
| 0 419 346 | 3/1991 | European Pat. Off. . |
| 0 500 472 | 8/1992 | European Pat. Off. . |
| 0 561 379 | 9/1993 | European Pat. Off. . |
| 03000 074 | 1/1989 | Japan . |
| 4-187206 | 7/1992 | Japan . |
| 05034337 | 2/1993 | Japan . |
| 05087808 | 4/1993 | Japan . |
| 05148150 | 6/1993 | Japan . |
| 05148151 | 6/1993 | Japan . |
| 5-194243 | 8/1993 | Japan . |
| WO9308904 | 11/1991 | WIPO . |
| WO9303740 | 3/1993 | WIPO . |

*Primary Examiner*—John Kim
*Attorney, Agent, or Firm*—Robert M. Barrett; Denise M. Serewicz; Bradford R. L. Price

[57] ABSTRACT

A leukodepletion filter is provided including glass fiber filter pads and non-woven polyester fiber filter pads sealed within a filter housing. The filter is designed such that a fluid, such as whole blood, packed red blood cells, platelets or plasma, is conducted through the glass fiber filter pads before the non-woven polyester fiber filter pads. A method is further provided for leukodepleting a body fluid by filtering the body fluid through glass fiber filter pads and also filtering the body fluid through non-woven polyester fiber filter pads. After filtering, the body fluid is collected.

17 Claims, 2 Drawing Sheets

U.S. PATENT DOCUMENTS

| | | | |
|---|---|---|---|
| 5,126,054 | 6/1992 | Matkovich | 210/436 |
| 5,128,048 | 7/1992 | Stewart et al. | 210/749 |
| 5,139,685 | 8/1992 | De Castro et al. | 210/767 |
| 5,190,657 | 3/1993 | Heagle et al. | 210/645 |
| 5,229,012 | 7/1993 | Pall et al. | 210/767 |
| 5,252,222 | 10/1993 | Matkovich et al. | 210/650 |
| 5,258,126 | 11/1993 | Pall et al. | 210/767 |
| 5,258,127 | 11/1993 | Gsell et al. | 210/767 |
| 5,298,165 | 3/1994 | Oka et al. | 210/505 |
| 5,454,946 | 10/1995 | Heagle et al. | 210/508 |

LEUKODEPLETION FILTER AND METHOD FOR FILTERING LEUKOCYTES FROM FRESHLY DRAWN BLOOD

BACKGROUND OF THE INVENTION

1. Field of the Invention

The invention generally relates to blood collection and processing. More particularly, the invention relates to filter devices and methods for removing leukocytes from whole blood and its components before transfusion or long term storage.

2. Description of the Prior Art

Most of the whole blood collected from donors today is not itself stored and used for transfusion. Instead, the whole blood is separated into its clinically proven components. These components include packed red blood cells, platelets and plasma. The components themselves are stored individually and used to treat a multiplicity of specific conditions and disease states.

In collecting whole blood components for transfusion, it is desirable to minimize the presence of impurities or other materials that may cause undesirable side effects in the recipient. For example, to reduce the transmission of disease and non-specific frebrile reactions, it is generally considered desirable to remove substantially all of the leukocytes from whole blood prior to transfusion, storage or separation into its clinically proven components.

In blood banks and hospitals, the most common way to remove leukocytes from whole blood is by filtration using a leukodepletion filter. Currently available leukodepletion filters employ various filtration media. One type of leukodepletion filter is fabricated from multiple, non-woven pads of melt-spun, polyester fibers, wherein the mean diameter of the fibers ranges from about 0.3 to about 3.0 micrometers. Commercially, a filter of this type is available from the Asahi Corporation, under the tradename designation Sepacell R 2000®.

It is well known in the industry that currently available leukodepletion filters are not effective in removing leukocytes from warm, freshly-drawn blood. To alleviate this problem, blood banks and hospitals allow blood to age 4 to 6 hours at ambient temperature or refrigerate the red cell concentrate fraction. One protocol requires that prior to filtration the red cell concentrate is held at 4° C. for twenty four (24) hours. Compared to warm blood, after the blood has been cooled, these filters typically display 1 to 3 orders of magnitude greater leukocyte depletion efficiency.

It would be advantageous to provide a leukodepletion filter which removes leukocytes equally well from warm, immediately-drawn blood (fresh) as from blood which has been cooled. Furthermore, it would be advantageous if the falter had a high capacity so that units of blood containing large numbers of leukocytes could be effectively leukodepleted using a single filter.

SUMMARY OF THE INVENTION

One aspect of the invention provides a leukodepletion filter. The filter of the invention includes a filter housing having an open space within. The housing has a filter inlet for conducting a body fluid into the open space and a filter outlet for conducting filtered body fluids out of the open space. A plurality of glass fiber filter pads are sealed within the open space of the filter housing. Preferably, the glass fibers have a mean diameter of from about 0.1 to about 5.0 micrometers. A plurality of non-woven polyester film filter pads is also sealed within the open space of the filter housing. Preferably the non-woven polyester fibers have a mean diameter of from about 0.1 to about 5.0 micrometers.

According to one embodiment, the glass fiber filter pads and the polyester fiber filter pads are sealed within the open space such that the body fluid which is conducted into the open space first contacts and passes through the glass fiber filter pads before contacting and passing through the polyester fiber filter pads.

Another aspect of the invention provides a method for leukodepleting a body fluid. The method comprises the steps of filtering the body fluid through a filter and collecting the filtered body fluid. According to one embodiment of the invention, the filter includes a filter housing having an open space within, a filter inlet for conducting the body fluid into the open space, and a filter outlet for conducting the filtered body fluid out of the open space; a plurality of glass fiber falter pads, sealed within the open spaces, wherein the glass fibers have a mean diameter of from about 0.1 to about 5.0 micrometers; and a plurality of non-woven, polyester fiber filter pads, sealed within the open space, wherein the non-woven polyester fibers have a mean diameter of from about 0.1 to about 5.0 micrometers.

According to one preferred embodiment of the invention, the glass fiber filter pads and the polyester fiber filter pads are sealed within the open space of the filter housing such that the body fluid which is conducted into the open space first contacts and passes through the glass fiber filter pads before contacting and passing through the polyester fiber filter pads. The filters of the invention further provide both good intrinsic leukodepletion efficiency and high capacity in warm, freshly-drawn blood for leukocytes.

DESCRIPTION OF THE PREFERRED EMBODIMENTS

Figure 1:
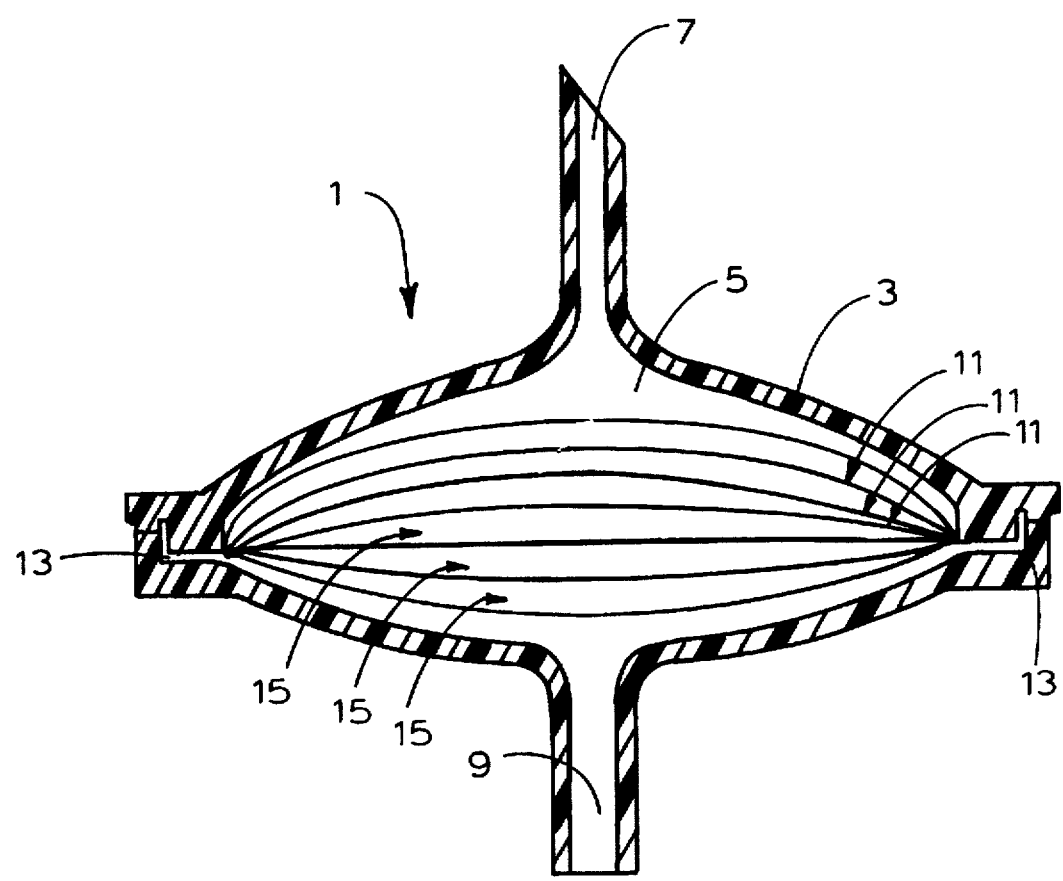
FIG. 1 is an enlarged sectional view of one embodiment of a filter incorporating the filter media of the invention.

The invention provides a leukodepletion filter that removes leukocytes equally well from warm, freshly-drawn blood as well as from blood which has been cooled. There are two attributes of a leukodepletion filter that determine its ability to remove leukocytes from blood: the intrinsic leukodepletion efficiency of the filter media and the leukodepletion capacity of the filter. The intrinsic leukodepletion efficiency is a measure of the optimum performance of a given filter media when challenged with a minimal number of leukocytes. The observed degree of leukodepletion is a function of the filter media architecture and surface composition. The second attribute, the leukodepletion capacity of a filter, describes the quantity of leukocytes that can be removed by a given filter assembly at the intrinsic efficiency of the media before allowing leukocytes to pass through the filter at a lesser leukodepletion efficiency and appear in the filtrate blood.

Currently, it is generally accepted that in order to increase the intrinsic leukodepletion efficiency of a given filter media to optimal levels, blood must be cooled, for example at 4° C. for twenty four (24) hours. Accordingly, it would be advantageous to provide a leukodepletion filter which would have its maximum intrinsic leukodepletion efficiency in warm blood, thereby obviating the step of cooling the blood. The step of cooling the blood is costly in both time and equipment and excludes leukodepletion of whole blood with recovery of non-activated platelets. Furthermore, it would be advantageous to provide a leukodepletion filter which has an increased leukodepletion capacity whereby units of blood containing an excessive number of leukocytes could be filtered through a single filter.

Lymphocytes and granulocytes are the two major cellular components of blood which, together, make up about ninety percent (90%) of the total leukocyte count. The inventors have discovered that polyester-based filters selectively remove lymphocytes from fresh, warm blood with both great efficiency and capacity for lymphocytes; but not for granulocytes. Current, commercially available polyester filters reduce total leukocyte content of fresh, warm blood by less than 4–5 $\log_{10}$. Furthermore, the inventors have discovered that glass filter media effectively removes both granulocytes and lymphocytes from blood immediately after collection with great efficiency, but does not have a great capacity for lymphocytes. Based on these discoveries, the inventors have combined polyester filter pads and glass filter pads in a filter, or in a series of filters, to remove the two components of leukocytes with great efficiency and great capacity. The filters of the invention have been demonstrated to leukodeplete a warm unit of whole blood by 5–6 $\log_{10}$ within one (1) hour after collection with filtration times under fifteen (15) minutes.

Furthermore, it has been discovered that the ratio of the filter media may be manipulated to improve the performance of the filter on both classes of leukocytes. Maximum leukodepletion capacity for a given filter design can be achieved by adjusting the relative quantities of the two media included in the filter assembly, such that both lymphocytes and granulocytes are detected in the blood filtrate in equal numbers when the capacity of the filter is exceeded.

The present invention provides a filter media and filter apparatus for leukodepleting whole blood and its clinically proven components. In more detail, referring to one embodiment of the invention shown in FIG. 1, the invention provides a filter 1 having a filter housing 3. The filter housing 3 includes an open space 5 within. The open space 5 is designed for receiving and sealing the filter media of the invention therein. The filter housing 3 includes a filter inlet 7 for conducting a body fluid into the open space 5 of the filter 1. The body fluid is preferably whole blood (warm or chilled), packed red blood cells (also referred to as red blood cell concentrate), or plasma and platelets (also referred to as platelet concentrate).

The filter housing 3 also includes a filter outlet 9 which conducts the body fluid (after filtration) out of the open space 5 and into a plastic medical tubing or the like (not shown). After the body fluid is filtered and exits the filter 1 via the filter outlet 9, the filtered body fluid is collected and stored. Preferably, the filtered body fluid is stored in a plastic medical solution container, such as a plastic blood bag.

A plurality of glass fiber filter pads 11 are sealed within the open space 5 of the filter housing 3. A seal 13 extends peripherally about the plurality of filter pads 11 and 15 and hermetically seals the falter pads 11 and 15 into the filter housing 3 such that no body fluids may pass around the filter pads 11 and 15, but instead, must pass through the filter pads 11 and 15.

The glass fiber filter pads 11 of the invention are fibrous, single-layer sheets made by a wet-laid paper-making process. The glass fibers of the invention preferably have a mean diameter of from about 0.1 to about 5 micrometers. More preferably, the glass fibers of the invention have a mean diameter of from about 0.3 to about 3 micrometers; and most preferably, the glass fibers of the invention have a mean diameter of from about 0.6 to about 1.8 micrometers. Preferred glass fiber sheets are commercially available from Ahlstrom Filtration Inc., under the product designations grade 142 and grade 144.

A plurality of non-woven polyester fiber filter pads 15 are also sealed within the open space 5 of the filter housing 3. The non-woven polyester fiber filter pads 15 of the invention are most preferably made from melt-spun polyester fibers. Commercially, melt-spun polyester fibers and polyester fiber filter pads are available from the Asahi Corporation under the tradename designations Sepacell R-2000, R-500 II and R-200. Preferably, the non-woven polyester fibers have a mean diameter of from about 0.1 to about 5.0 micrometers. More preferably, the non-woven polyester fibers have a mean diameter of from about 0.3 to about 3.0 micrometers; and most preferably, the non-woven polyester fibers have a mean diameter of from about 0.3 to about 0.8 micrometers.

According to one preferred embodiment of the invention, as shown in FIG. 1, the glass fiber filter pads 11 and the polyester fiber filter pads 15 are sealed within the open space 5 such that the body fluid which is conducted via the inlet 7 into the open space 5 first contacts and passes through the glass fiber filter pads 11 before contacting and passing through the polyester fiber filter pads 15. This is a preferred arrangement since the glass fiber filter pad 15 may shed glass fibers which will be filtered and held by the polyester fiber filter pads 15 beneath. This arrangement prevents irritation to the patient's vasculature and other possible complications. Nevertheless, the preferred glass fiber filter pads of the invention, obtained from Ahlstrom Filtration Inc., are precoated with polyvinyl alcohol to reduce fiber shedding.

As discussed above, the ratio of the glass filter pads to the polyester filter pads may be varied to more efficiently leukodeplete. Preferably, the weight ratio of the glass fiber filter pads 11 to the polyester fiber filter pads 15 is from about 3:1 to about 1:20. More preferably, the ratio of the glass fiber filter pads 11 to the polyester fiber filter pads 15 is from about 1:1 to about 1:10, and most preferably, the ratio of the glass fiber filter pads 11 to the polyester fiber filter pads 15 is from about 1:2 to about 2:5.

As previously discussed, one important advantage of the invention is that the filters of the invention leukodeplete warm as well as chilled body fluids. According to one embodiment of the invention, the body fluid is preferably whole blood or packed red blood cells and has a temperature of from about 20° C. to about 38° C. More preferably, the body fluid has a temperature of from about 25° C. to about 34° C.; and most preferably, the body fluid has a temperature of from about 28° C. to about 32° C.

The filter media and filters of the invention are useful for leukodepleting fresh, warm body fluids and may be used immediately after the blood has been collected or during the blood collection process. According to one embodiment of the invention, a filter of the invention is used at a donor's bedside during blood collection and is disposed between the donor from which blood is being collected and the storage container in which the filtered blood is being stored.

It should be noted that the filter shown in FIG. 1 is one embodiment of the invention and any filter configuration using the media described herein is within the scope of the invention. According to another preferred embodiment, the invention provides a method for leukodepleting body fluid wherein a body fluid is passed through a first filter including a plurality of glass fiber filter pads, sealed within a filter. Once filtered by the first filter, the blood is then passed through a second filter including a plurality of non-woven polyester fiber filter pads. According to this embodiment, the blood passes from the first filter to the second filter via a medical tubing. After the blood passes through the second filter, the blood is collected in a storage container for storage or separation.

EXAMPLES

CPDA-1 anticoagulated whole blood was used in these examples and was obtained in conformance with American Association of Blood Bank standards. Blood was drawn from donors who had been tested for the presence of infectious agents prior to the collection. Leukocyte counts were made either by Sysmex K-1000 automatic blood cell counters for leukocyte counts greater than 0.5 million per milliliter, or by a flow cytometric method (Vachula, et al.: Transfusion 33 (1993) 262–267) for leukocyte concentrations between 10 per milliliter and 0.5 million per milliliter. Differential leukocyte counts to determine the percentage of the various white cell species was performed by Sysmex K-1000 for leukocyte counts greater than one million per milliliter and by a flow cytometric method (Steinkamp et al.: Acta Cytologica 17 (1973) 113–117) for white cell counts less than one million per milliliter and greater than ten per milliliter.

Example 1

Figure 2:
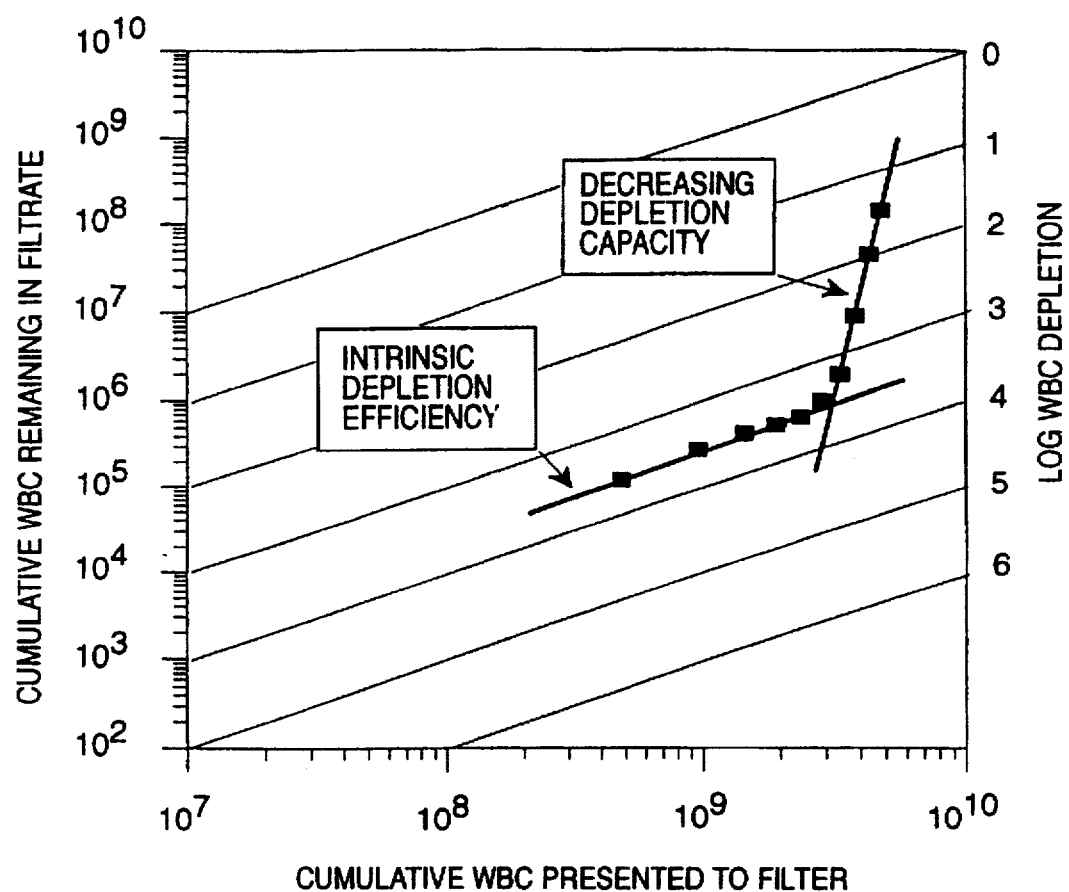
FIG. 2 is a log-log graph of leukocytes recovered in the filtrate.

Method to quantify the intrinsic cell capture efficiency and the capacity of leukodepletion filters. Two units of blood drawn from ABO/Rh-compatible donors were held at 23° C. for 24 hours, then mixed and filtered through an RC-400 filter (Pall Biomedical Products, East Hills, N.Y.). The blood was collected at the filter outlet in 10–100 ml fractions and the leukocytes in each fraction counted by flow cytometry. The cumulative total of leukocytes (WBC) presented to the filter as whole blood and the cumulative total WBC recovered in the filtrate were plotted on a log-log graph, on which diagonal lines denote constant log depletion (FIG. 2). The data showed a biphasic curve of two straight lines. The initial and subsequent fractions were leukodepleted at a constant maximum log depletion value, until, at a given quantity of WBC presented to the filter, the log WBC depletion fell off linearly. The initial straight isodepletion line defines the intrinsic cell capture efficiency of the filter media; while the intersection of the two fine segments indicates a filter capacity function. The second straight line represents a decreasing capacity for leukodepletion by the filter.

Example 2

Preferential depletion of leukocyte species by glass and polyester filter media. Filter media from a commercial leukodepletion filter, R-2000 (Asahi Medical Corporation, Tokyo, Japan) containing melt-spun polyester fiber mats with mean fiber diameter in the range 0.3 to 3 micrometers, or glass fiber filter paper (No. 142: Ahlstrom Filtration Inc. Mt. Holly Springs, Pa.) with mean fiber diameter 0.6 to 1.8 micrometers were placed in a 3.2 cm diameter pediatric-size filter housings. Whole blood that had been drawn two hours prior to the experiment was passed through the filters. The filtered blood was collected in 10 mL fractions and the leukocyte count in each fraction was determined. Analysis of the leukocyte differential counts in the filtered blood showed that the polyester filter preferentially removed lymphocytes, whereas the glass filter predominantly captured granulocytes and monocytes. This bias was displayed from the inception of filtration until the capacity of the filter to deplete leukocytes was approached.

Example 3

Effect of glass:polyester ratio in filter pads on leukodepletion. Filter pads of polyester and glass filter media as in Example 2 were combined in different ratios and sealed in 3.2 cm diameter pediatric-size filter housings. Whole blood that had been drawn 1–2 hours prior to the experiment was passed through the filters at a rate of about 10 ml/min. The filtered blood was collected in discrete fractions and the leukocyte count determined in each fraction. The data for each filter was graphed as in Example 1 and the cumulative WBC remaining in the filtered blood after $2\times10^8$ WBC had been presented to each filter was determined from the graph and summarized as Table 1. The challenge value of $2\times10^8$ WBC was chosen because it was in the decreasing capacity region for all filters. The initial addition of glass media to the polyester filter was sufficient to attain the full leukodepletion effect on warm, freshly drawn blood under these conditions; however, the balance between granulocyte and lymphocyte capture by the filter occurred at the next higher glass:polyester ratio.

TABLE 1

| Glass:Polyester Ratio (Weight:Weight) | Cumulative WBC in Filtrate | Log WBC Depletion | Lymphocyte:Granulocyte Radio in Filtrate |
|---|---|---|---|
| 0:100 | $1.6 \times 10^6$ | 2.1 | 23:77 |
| 15:85 | $2.0 \times 10^5$ | 3.0 | 10:90 |
| 33:67 | $2.5 \times 10^5$ | 2.9 | 85:15 |
| 53:47 | $2.5 \times 10^5$ | 2.9 | 94:6 |
| 75:25 | $1.6 \times 10^5$ | 3.1 | 75:25 |

Example 4

Improved leukodepletion of freshly drawn blood by combined glass and polyester filter media. Full units of blood were drawn and filtered at ambient temperature within one hour (Asahi R2000) or two hours (Pall BPF4) through commercially available leukodepletion filters, alone or connected in series to a 5.1 cm diameter filter containing 5 glass filter pads (Grade 142, Ahlstrom Filtration). This constitutes a glass:polyester weight ratio of 27:73 for the Asahi R2000. The blood was collected at the filter outlet in 5–100 ml fractions and the leukocytes in each fraction counted by flow cytometry. The data was evaluated as in Example 1 and is given in Table 2.

TABLE 2

| Filter | Number of Trials | Total WBC in Filtered Unit Mean ± Std. Dev. or *Actual Values | Log WBC Depletion |
|---|---|---|---|
| Asahi R2000 | 6 | $6.5 \times 10^7 \pm 2.0 \times 10^7$ | $1.5 \pm 0.2$ |
| Asahi R2000 plus glass | 9 | $1.4 \times 10^4 \pm 0.7 \times 10^4$ | $5.2 \pm 0.3$ |
| Pall BPF4 | 2 | *$1.5 \times 10^7$, $1.5 \times 10^6$ | 2.2, 3.1 |
| Pall BPF4 plus glass | 2 | *$5.3 \times 10^4$, $1.0 \times 10^4$ | 4.7, 5.2 |

We claim:

1. A leukodepletion filter comprising:
   a) a filter housing having an open space within, a filter inlet for conducting a body fluid into the open space and a filter outlet for conducting the body fluid out of the open space;

b) a plurality of glass fiber filter pads, sealed within the open space of the filter housing, wherein the glass fibers have a mean diameter of from about 0.1 to about 5.0 micrometers; and c) a plurality of non-woven polyester fiber filter pads, sealed within the open space of the filter housing, wherein the non-woven polyester fibers have a mean diameter of from about 0.1 to about 5.0 micrometers wherein the glass fiber filter pads and the polyester fiber filter pads are sealed within the open space such that the body fluid which is conducted into the open space first contacts and passes through the glass fiber filter pads before contacting and passing through the polyester fiber filter pads.

2. The filter of claim 1 wherein the glass fibers have a mean diameter of from about 0.3 to about 3.0 micrometers, and the polyester fibers have a mean diameter of from about 0.3 to about 3.0 micrometers.

3. The filter of claim 1 wherein the glass fibers have a mean diameter of from about 0.6 to about 1.8 micrometers, and the polyester fibers have a mean diameter of from about 0.3 to about 0.8 micrometers.

4. A method for leukodepleting a body fluid, the method comprising the steps of:

a) filtering the body fluid through a filter comprising a filter housing having an open space within, a filter inlet for conducting the body fluid into the open space, and a filter outlet for conducting the body fluid out of the open space; a plurality of glass fiber filter pads, sealed within the open space near the filter inlet, wherein the glass fibers have a mean diameter of from about 0.1 to about 5.0 micrometers; and a plurality of non-woven polyester fiber filter pads, sealed within the open space, near the filter outlet, wherein the non-woven polyester fibers have a mean diameter of from about 0.1 to about 5.0 micrometers and further wherein the glass fiber filter pads and the polyester fiber filter pads are sealed within the open space of the filter housing such that the body fluid which is conducted into the open space first contacts and passes through the glass fiber filter pads before contacting and passing through the polyester fiber filter pads; and b) collecting the filtered body fluid.

5. The method of claim 4 wherein the glass fibers have a mean diameter of from about 0.3 to about 3.0 micrometers, and the polyester fibers have a mean diameter of from about 0.3 to about 3.0 micrometers.

6. The method of claim 4 wherein the glass fibers have a mean diameter of from about 0.6 to about 1.8 micrometers, and the polyester fibers have a mean diameter of from about 0.3 to about 0.8 micrometers.

7. The method of claim 4 wherein the body fluid is selected from the group consisting of whole blood, packed red blood cells, platelets and plasma.

8. The method of claim 4 wherein the body fluid is fresh, warm whole blood or warm packed red blood cells having a temperature of from about 20° to about 38° C.

9. A method of leukodepleting fresh, warm whole blood, the method comprising the step of:

a) passing the whole blood through a filter comprising a filter housing having an open space within, a filter inlet for conducting the whole blood into the open space, and a filter outlet for conducting the whole blood out of the open space; a plurality of glass fiber pads, sealed within the open space, wherein the glass fibers have a mean diameter of from about 0.1 to about 5.0 micrometers; and a plurality of non-woven polyester fiber filter pads, sealed within the open space, wherein the non-woven polyester fibers have a mean diameter of from about 0.1 to about 5.0 micrometers and further wherein the glass fiber filter pads and the polyester fiber filter pads are sealed within the open space such that the whole blood which is conducted into the open space first contacts and passes through the glass fiber filter pads before contacting and passing through the polyester fiber filter pads.

10. The method of claim 9 wherein the glass fibers have a mean diameter of from about 0.3 to about 3.0 micrometers, and the polyester fibers have a mean diameter of from about 0.3 to about 3.0 micrometers.

11. The method of claim 9 wherein the glass fibers have a mean diameter of from about 0.6 to about 1.8 micrometers, and the polyester fibers have a mean diameter of from abut 0.3 to about 0.8 micrometers.

12. The method of claim 9 wherein the warm whole blood has a temperature of from about 20° to 38° C.

13. A method for leukodepleting a body fluid, the method comprising the steps of:

a) filtering the body fluid through a first filter comprising a filter housing having therein a plurality of glass fiber filter pads, wherein the glass fibers have a mean diameter of from about 0.1 to about 5.0 micrometers; and b) filtering the body fluid through a second filter comprising a filter housing having therein a plurality of non-woven polyester filter pads, wherein the non-woven polyester fibers have a mean diameter of from about 0.1 to about 5.0 micrometers and further wherein the filtering through the first filter is conducted prior to the filtering through the second filter.

14. The method of claim 13 wherein the glass fibers have a mean diameter of from about 0.3 to about 3.0 micrometers, and the polyester fibers have a mean diameter of from about 0.3 to about 3.0 micrometers.

15. The method of claim 13 wherein the glass fibers have a mean diameter of from about 0.6 to 1.8 micrometers, and the polyester fibers have a mean diameter of from about 0.3 to about 0.8 micrometers.

16. The method of claim 13 wherein the body fluid is selected from the group consisting of whole blood, packed red blood cells, platelets and plasma.

17. The method of claim 13 wherein the body fluid is fresh, warm whole blood or warm packed red blood cells having a temperature of from about 20° to about 38° C.

* * * * *